(12) United States Patent
Maruyama et al.

(10) Patent No.: US 8,900,122 B2
(45) Date of Patent: Dec. 2, 2014

(54) ENDOSCOPE APPARATUS

(75) Inventors: Koji Maruyama, Hachioji (JP); Takashi Suzuki, Chofu (JE)

(73) Assignee: Olympus Corporation, Tokyo (JP)

( * ) Notice: Subject to any disclaimer, the term of this patent is extended or adjusted under 35 U.S.C. 154(b) by 1208 days.

(21) Appl. No.: 12/024,386

(22) Filed: Feb. 1, 2008

(65) Prior Publication Data

US 2008/0207993 A1  Aug. 28, 2008

(30) Foreign Application Priority Data

Feb. 28, 2007 (JP) .................... 2007-050633

(51) Int. Cl.
A61B 1/00 (2006.01)
G02B 23/24 (2006.01)
A61B 1/12 (2006.01)

(52) U.S. Cl.
CPC ........ *A61B 1/00105* (2013.01); *G02B 23/2476* (2013.01); *A61B 1/128* (2013.01)
USPC .......................................... 600/102; 600/101

(58) Field of Classification Search
USPC .......................... 600/101, 132, 178, 179, 102; 361/679.45–679.54
See application file for complete search history.

(56) References Cited

U.S. PATENT DOCUMENTS

| | | | | | |
|---|---|---|---|---|---|
| 4,113,589 | A | * | 9/1978 | Leach | 204/157.5 |
| 4,933,816 | A | * | 6/1990 | Hug et al. | 362/551 |
| 5,469,841 | A | * | 11/1995 | Kobayashi et al. | 600/158 |
| 5,973,920 | A | * | 10/1999 | Altic et al. | 361/679.26 |
| 2002/0141152 | A1 | * | 10/2002 | Pokharna et al. | 361/687 |
| 2004/0054259 | A1 | * | 3/2004 | Hasegawa et al. | 600/152 |
| 2004/0158128 | A1 | * | 8/2004 | Fujikawa et al. | 600/132 |
| 2005/0105267 | A1 | * | 5/2005 | Cheng | 361/690 |
| 2005/0245789 | A1 | * | 11/2005 | Smith et al. | 600/159 |
| 2006/0015012 | A1 | * | 1/2006 | Sato | 600/118 |
| 2006/0225441 | A1 | * | 10/2006 | Goenka et al. | 62/115 |
| 2007/0015966 | A1 | * | 1/2007 | Niwa et al. | 600/115 |
| 2009/0146583 | A1 | * | 6/2009 | Bhadri et al. | 315/294 |

FOREIGN PATENT DOCUMENTS

| | | |
|---|---|---|
| JP | 2000-089131 | 3/2000 |
| JP | 2003-294921 | 10/2003 |
| JP | 2004-126570 | 4/2004 |
| JP | 2004-283484 | 10/2004 |
| JP | 3111112 | 5/2005 |
| JP | 2005-177134 | 7/2005 |
| JP | 2006-218203 A | 8/2006 |

OTHER PUBLICATIONS

Japanese Office Action dated Nov. 22, 2011, issued to counterpart Japanese Patent Application No. 2007-050633.

* cited by examiner

*Primary Examiner* — Anhtuan T Nguyen
*Assistant Examiner* — Rynae Boler
(74) *Attorney, Agent, or Firm* — Scully, Scott, Murphy & Presser, PC

(57) ABSTRACT

An endoscope apparatus according to the present invention is featured by including: an endoscope which has a connector main body; an apparatus main body to which the connector main body can be detachably mounted; a closed space which, after the connector main body is mounted to the apparatus main body, is formed in exterior housings of the apparatus main body and the connector main body by being closed by the exterior housings; a heat generating portion which is provided in the closed space; and a fan which is provided in the closed space, and performs at least one of dissipation of heat of the heat generating portion to the closed space and transfer of heat in the atmosphere in the closed space to the exterior housing.

15 Claims, 13 Drawing Sheets

ENDOSCOPE APPARATUS

CROSS REFERENCE TO RELATED APPLICATION

This application claims benefit of Japanese Patent Application No. 2007-050633 filed in Japan on Feb. 28, 2007, the contents of which are incorporated by this reference.

BACKGROUND OF THE INVENTION

1. Field of the Invention

The present invention relates to an endoscope apparatus including an apparatus main body and an endoscope having a connector main body which can be freely attached and detached to and from the apparatus main body.

2. Description of the Related Art

As is well known, endoscope apparatuses have been widely used in medical fields and industrial fields. An endoscope apparatus used in a medical field is capable of observing an organ in a body cavity by inserting a thin and long insertion portion of an endoscope into the body cavity, and performing various medical treatments by using a treatment instrument inserted in a treatment instrument insertion channel as required.

Further, an endoscope apparatus used in an industrial field is capable of performing observation, various treatment, and the like, of damage, corrosion, and the like, of parts to be inspected by inserting a thin and long insertion portion of an endoscope into the inside of a jet engine, a pipe in a plant, and the like.

Therefore, the industrial endoscope apparatus is generally used in an outdoor working facility, a working facility in a plant, and the like. As the industrial endoscope apparatus, there are known, for example, a large-sized endoscope apparatus which has an insertion portion of 10 m in length, and a shoulder type small endoscope apparatus which has an insertion portion of 3 m in length and is excellent in portability.

The industrial endoscope apparatus is generally configured by an endoscope having a thin and long insertion portion at a distal end of which an image pickup unit, or the like, is arranged, and an apparatus main body to which the endoscope is connected. Further as the small industrial endoscope apparatus, there is also known an endoscope apparatus in which a light source, such as an LED, is arranged at a distal end thereof.

Further, in the apparatus main body, there are arranged various members for driving the endoscope, such as specifically, electrical components such as an image processing unit which drives an image pickup unit and performs processing on a subject image signal outputted from the image pickup unit, and a battery unit of the endoscope apparatus. For example, an electrical component arranged in the apparatus main body serves as a heat generating portion which generates heat when electric power is supplied.

Here, when the electrical component generates heat by the driving of the endoscope and is heated up to a certain fixed temperature or higher, not only is the atmosphere in the exterior housing excessively heated, but also the reliability of the electrical components is deteriorated. Specifically, such excessive heating may result in malfunction of the electrical components, internal destruction of the electrical components, or a short-circuit in the electrical components.

For this reason, the reliability of the electrical components is generally prevented from being deteriorated by such a way that a plurality of holes are provided in the exterior housing of the apparatus main body and cooling fans are respectively provided in correspondence with the plurality of holes in the apparatus main body, and that the atmosphere in the apparatus main body is cooled by using the fans for taking outside air into the apparatus main body through the plurality of holes serving as air inlet ports, and for discharging the atmosphere in the apparatus main body to the outside of the apparatus main body through the plurality of holes serving as air outlet ports.

Further, as described above, the industrial endoscope apparatus is generally used in an outdoor working facility, or a working facility in a plant, and the like. Therefore, when the plurality of holes are provided in the exterior housing, foreign matters, such as dust, in the outside air enter into the apparatus main body from the plurality of holes. When the foreign matters are deposited in the apparatus main body, ventilation between the air inlet port and the air outlet port becomes poor. Further, when the foreign matters are iron powder and the like, there may be a case where the insulating state of the electrical components is deteriorated, thereby causing a short circuit, and the like.

In view of the above described circumstances, there is proposed, in Japanese Patent Laid-Open No. 2004-283484, an endoscope apparatus configured such that dustproof filters are respectively provided near the plurality of holes in the apparatus main body in correspondence with the plurality of holes, together with a cooling fan, so as to trap, by the dustproof filters, foreign matters, such as dust, entering into the apparatus main body.

SUMMARY OF THE INVENTION

Simply, an endoscope apparatus according to the present invention includes: an endoscope which is provided with a connector main body; an apparatus main body to which the connector main body can be detachably mounted; a closed space which after the connector main body is mounted to the apparatus main body, is formed in exterior housings of the apparatus main body and the connector main body by being closed by the exterior housings; a heat generating portion which is provided in the closed space; and a fan which is provided in the closed space, and which performs at least one of dissipation of heat of the heat generating portion to the closed space, and transfer of heat in the atmosphere in the closed space to the exterior housing.

Further, an endoscope apparatus according to the present invention includes: an endoscope which is provided with a connector main body; an apparatus main body to which the connector main body can be detachably mounted; a closed space which after the connector main body is mounted to the apparatus main body, is formed in exterior housings of the apparatus main body and the connector main body by being closed by the exterior housings; a heat generating portion which is provided in the closed space; and a heat diffusion member which is provided in the closed space, and which performs at least one of dissipation of heat of the heat generating portion to the closed space, and transfer of heat in the atmosphere in the closed space to the exterior housing.

Further, an endoscope apparatus according to the present invention is featured by including: an endoscope which has a connector main body; an apparatus main body to which the connector main body is mounted; a closed space which is formed by the apparatus main body and the connector main body; a heat generating portion which is provided in the closed space; and heat dissipating means which is provided in the closed space, and which performs at least one of dissipation of heat of the heat generating portion to the closed space, and transfer of heat in the atmosphere in the closed space to the exterior housing.

The above and other objects, feature and advantages of the invention will become more clearly understood from the following description referring to the accompanying drawings.

DETAILED DESCRIPTION OF THE PREFERRED EMBODIMENTS

In the following, embodiments according to the present invention will be described with reference to the accompanying drawings. In the following embodiments, an endoscope apparatus will be described by taking as an example a shoulder type industrial endoscope apparatus which is excellent in portability.

First Embodiment

Figure 1:
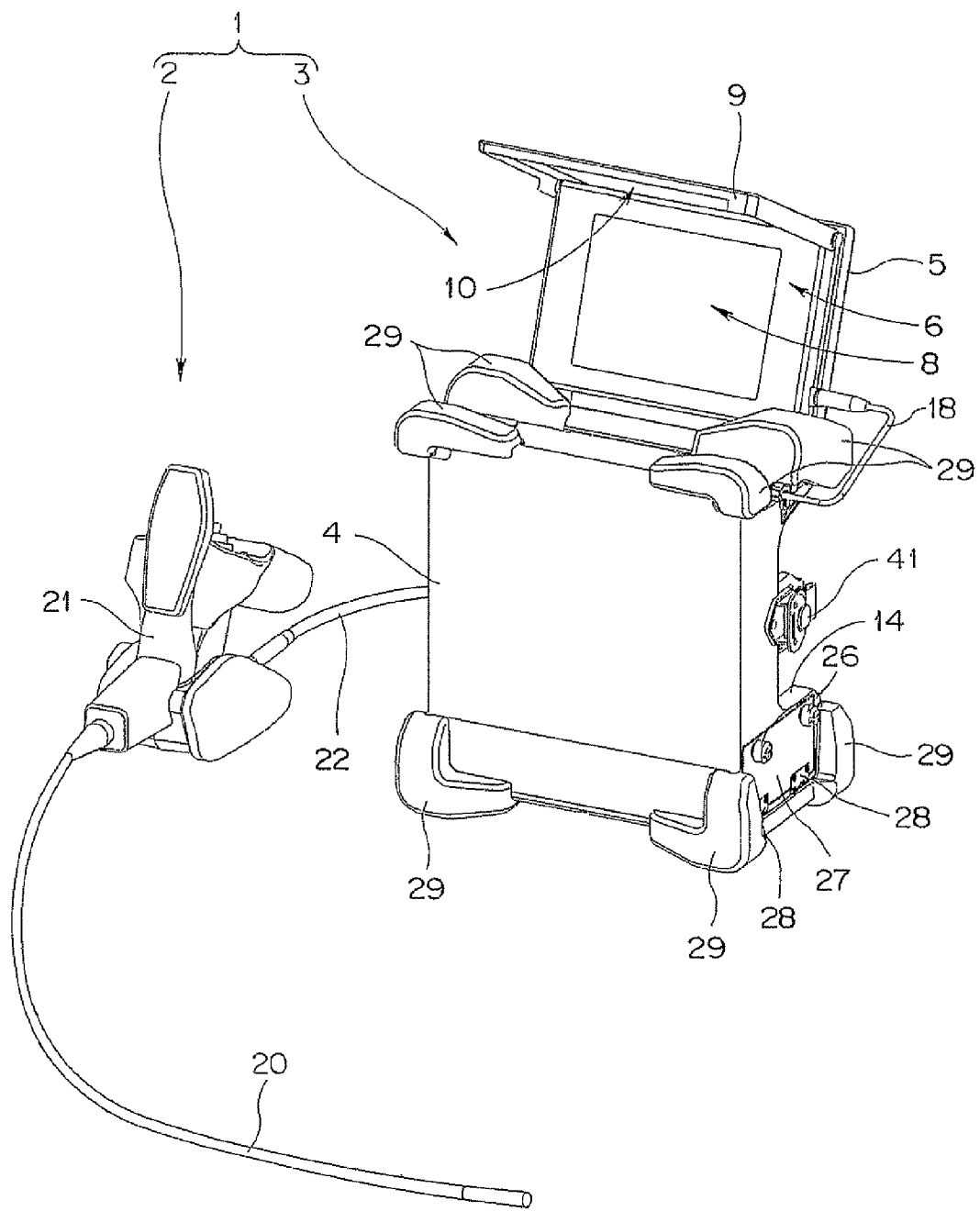
FIG. 1 is a perspective view showing an endoscope apparatus according to a first embodiment in a state where a monitor is rotated and raised from an apparatus main body.
Figure 2:
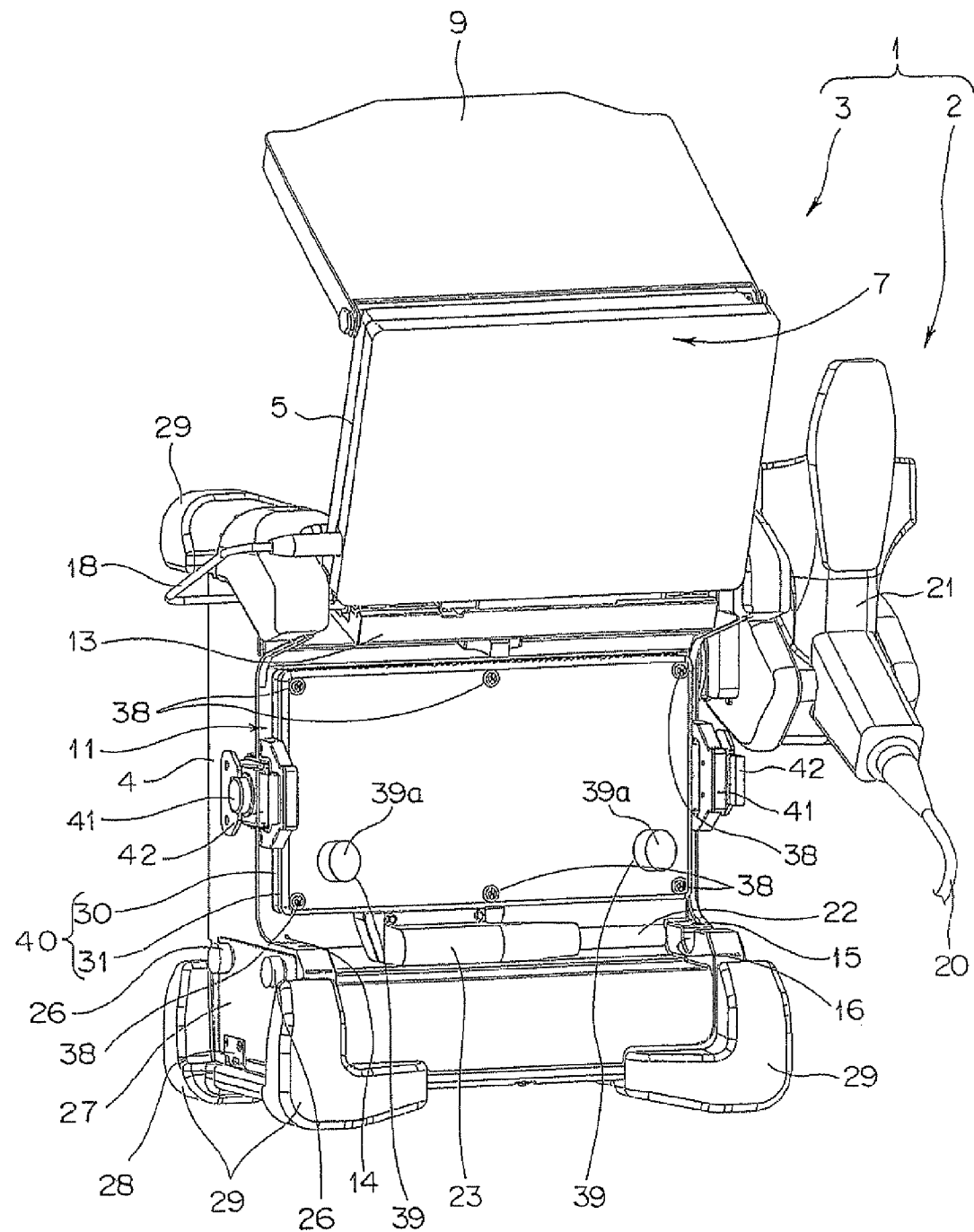
FIG. 2 is a perspective view of the endoscope apparatus seen from a rear side of the apparatus main body of FIG. 1.
Figure 3:
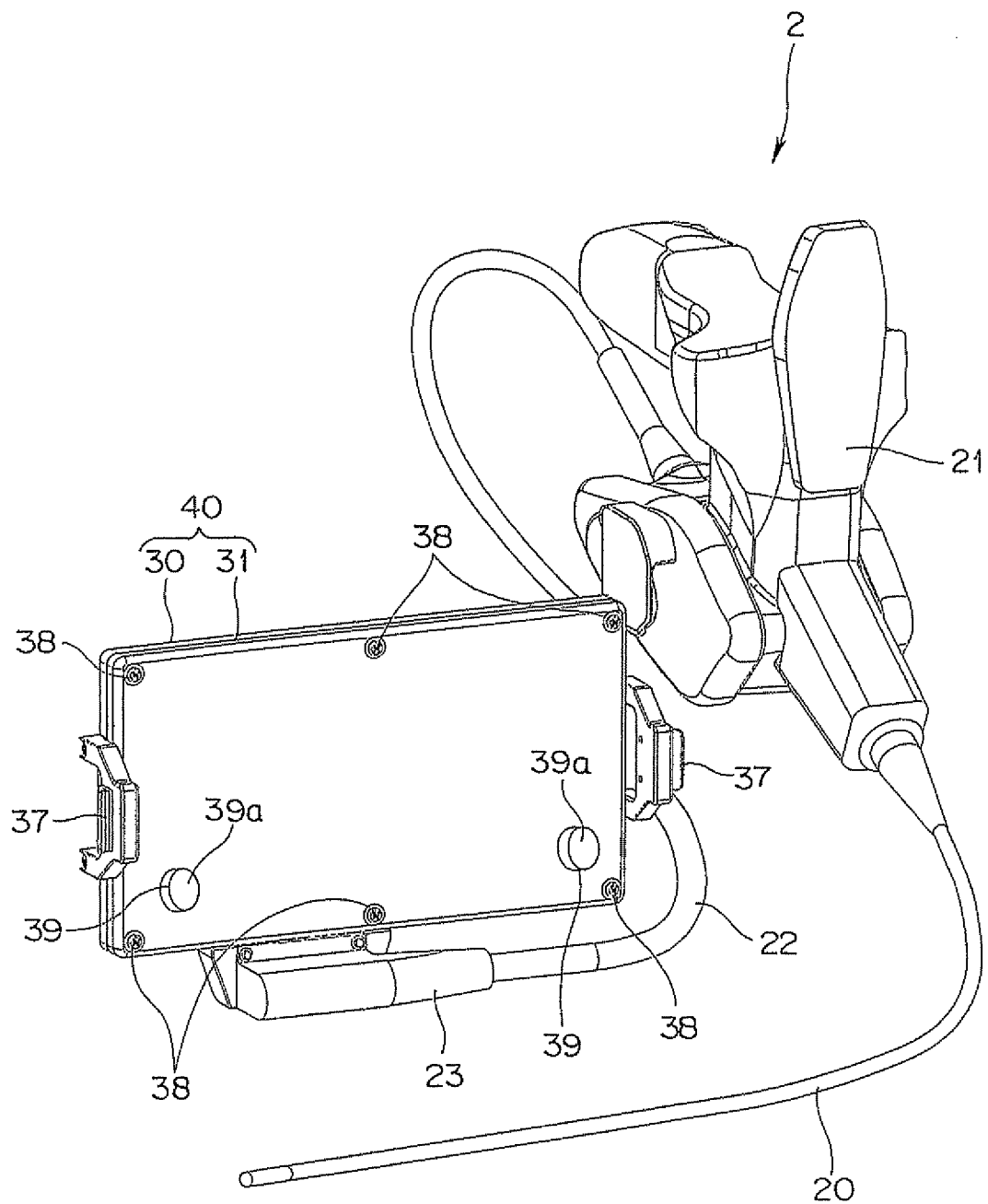
FIG. 3 is a perspective view of the endoscope, showing a state where the endoscope is removed from the apparatus main body of FIG. 2.

FIG. 1 is a perspective view showing an endoscope apparatus according to a first embodiment in a state where a monitor is rotated and raised from an apparatus main body. FIG. 2 is a perspective view of the endoscope apparatus seen from a rear side of the apparatus main body of FIG. 1. FIG. 3 is a perspective view of the endoscope, showing a state where the endoscope is removed from the apparatus main body of FIG. 2.

Figure 4:
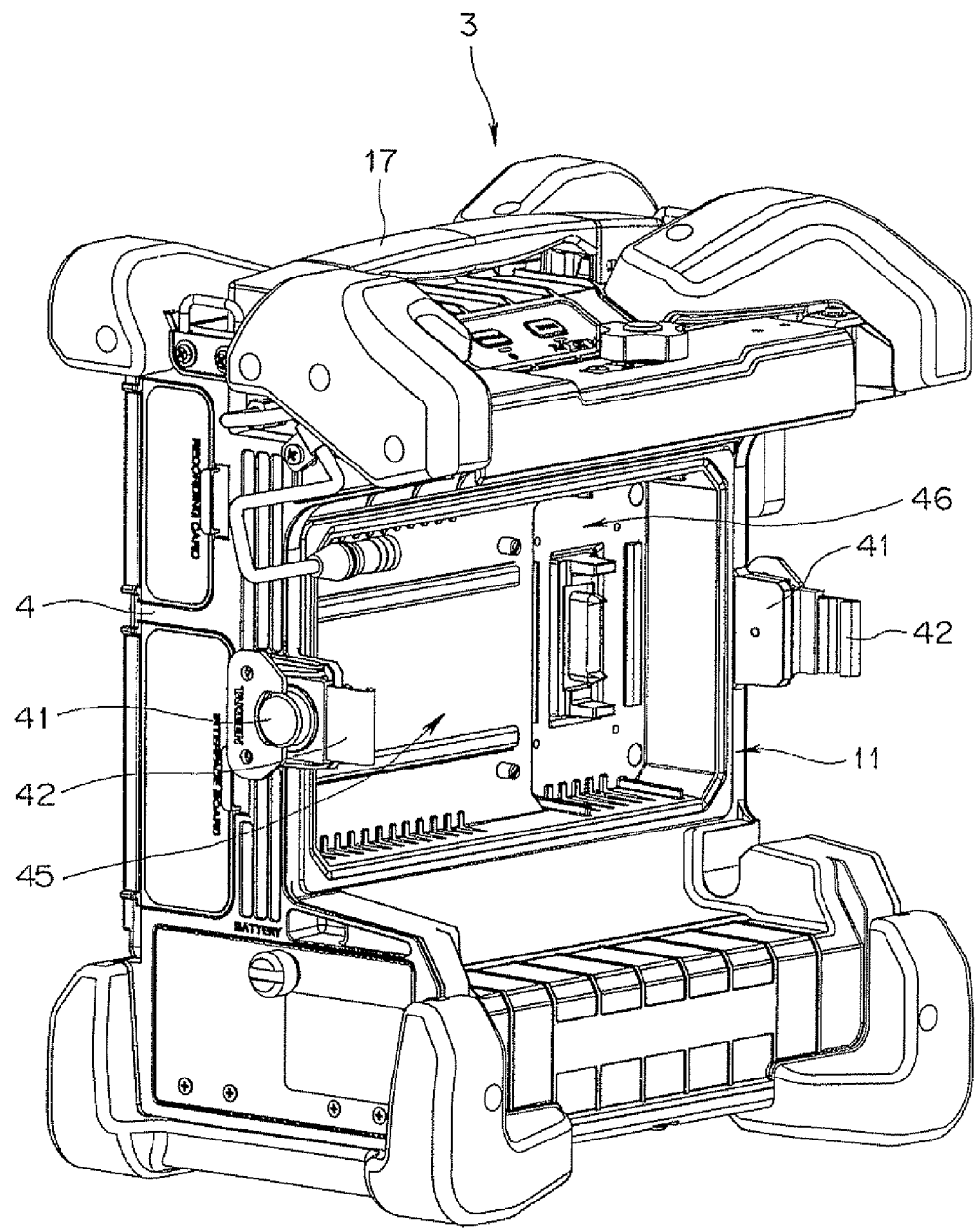
FIG. 4 is a perspective view of the apparatus main body from which the endoscope of FIG. 2 is removed.
Figure 5:
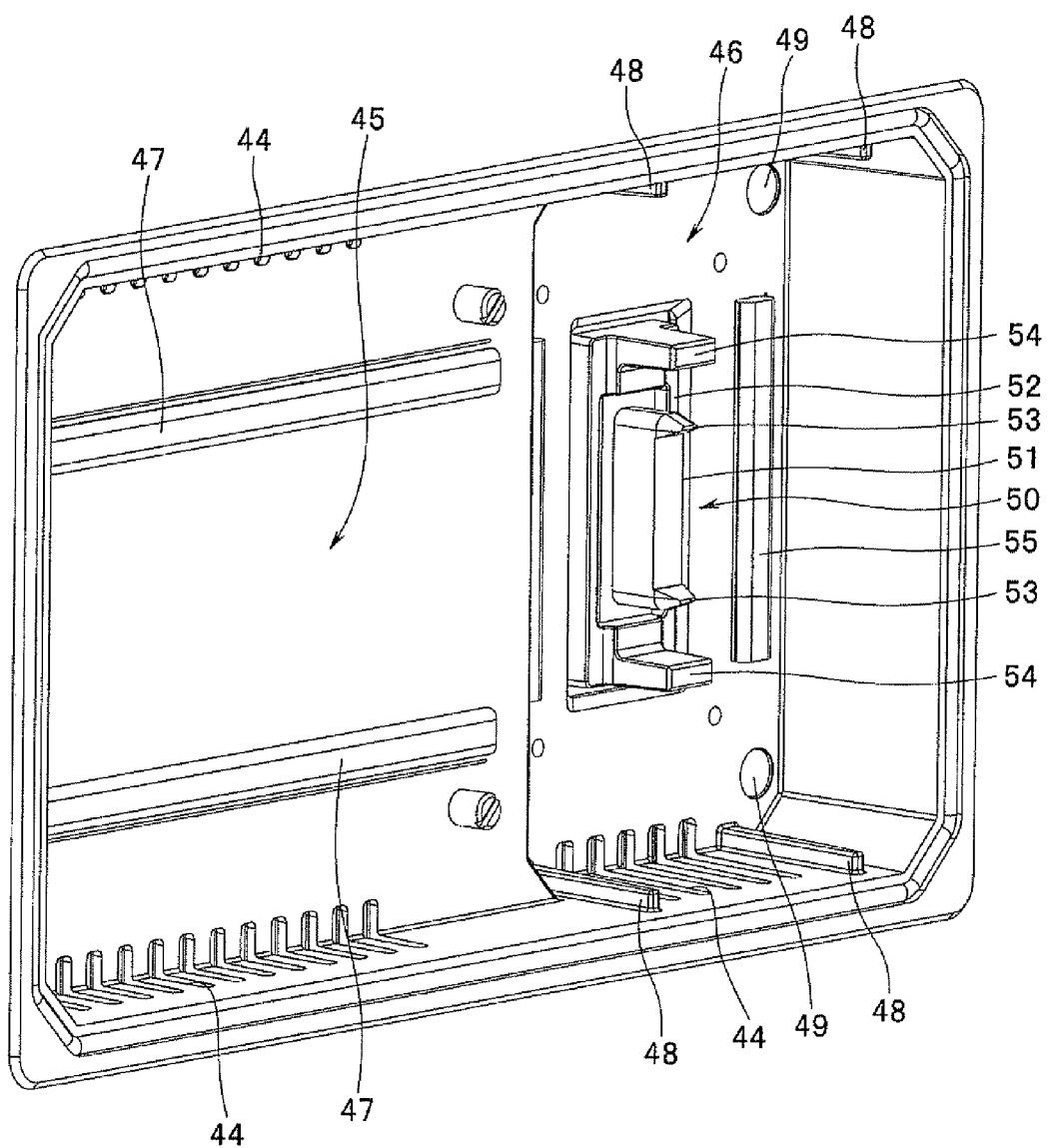
FIG. 5 is an enlarged perspective view showing a connector box housing chamber of the apparatus main body of FIG. 4.
Figure 6:
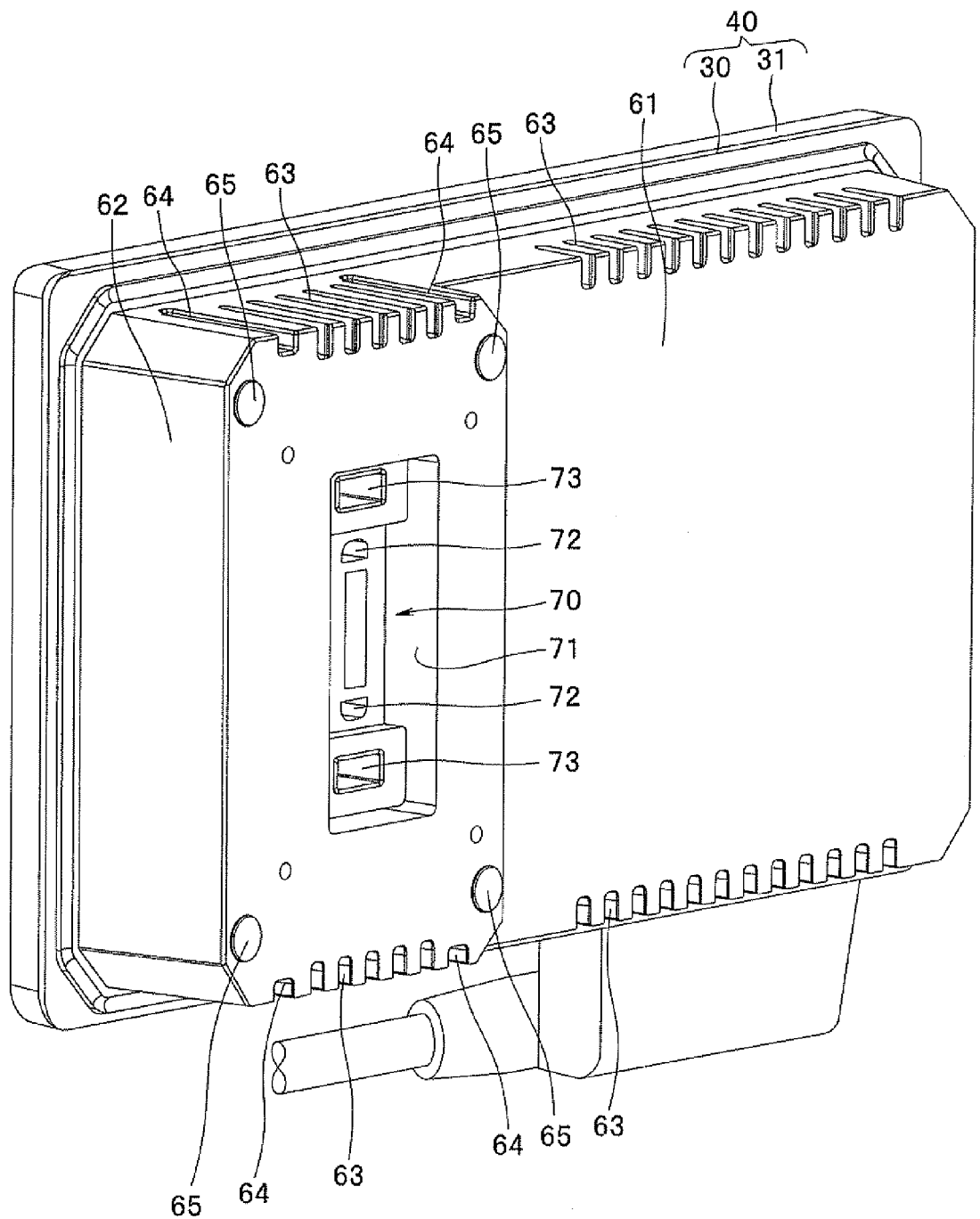
FIG. 6 is an enlarged perspective view showing a rear side of a connector box of the endoscope of FIG. 3.

Further, FIG. 4 is a perspective view of the apparatus main body from which the endoscope of FIG. 2 is removed. FIG. 5 is an enlarged perspective view showing a connector box housing chamber of the apparatus main body of FIG. 4. FIG. 6 is an enlarged perspective view showing a rear side of a connector box of the endoscope of FIG. 3.

Figure 7:
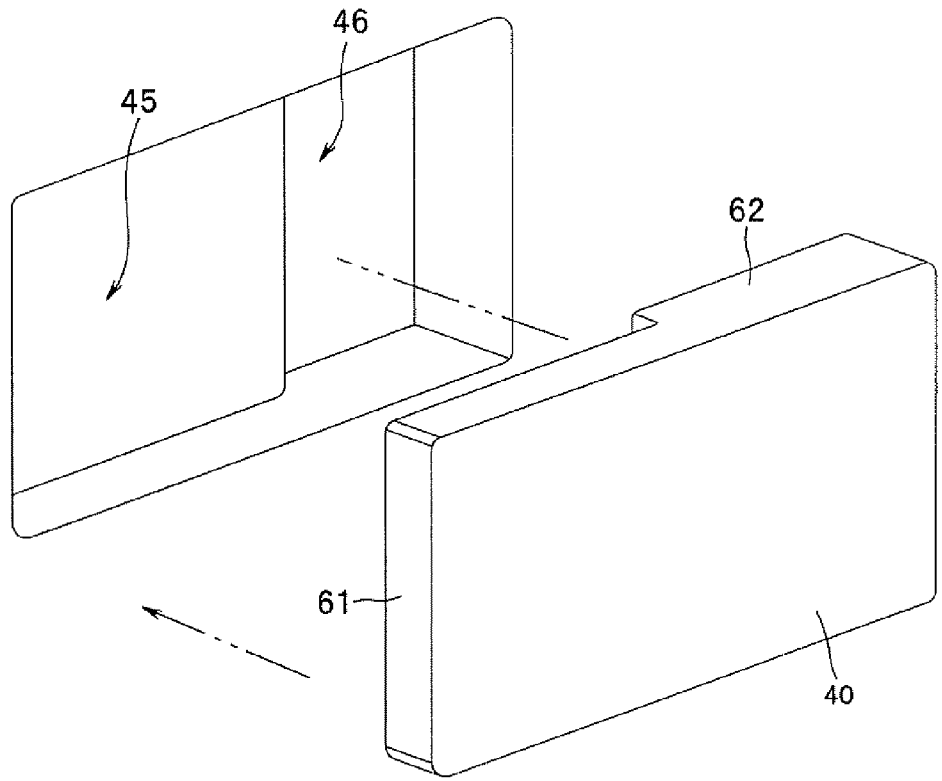
FIG. 7 is a figure schematically showing a state before the connector box is mounted to the connector box housing chamber.
Figure 8:
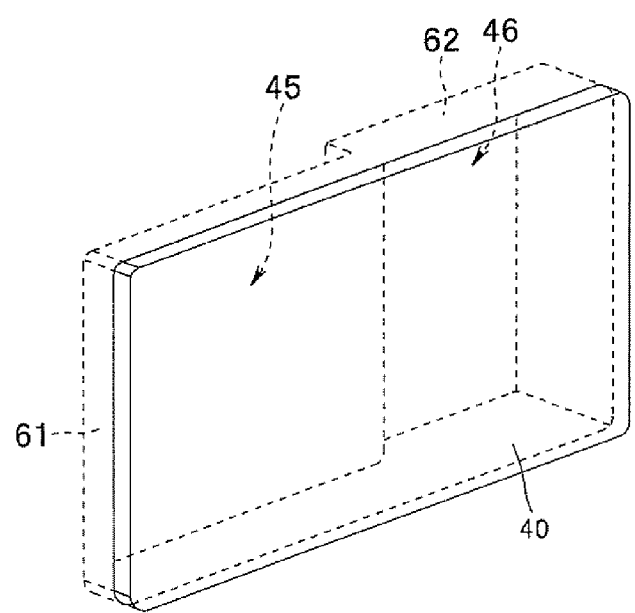
FIG. 8 is a figure schematically showing a state where the connector box is mounted to the connector box housing chamber of FIG. 7.

Further, FIG. 7 is a figure schematically showing a state before the connector box is mounted to the connector box housing chamber. FIG. 8 is a figure schematically showing a state where the connector box is mounted to the connector box housing chamber.

Figure 9:
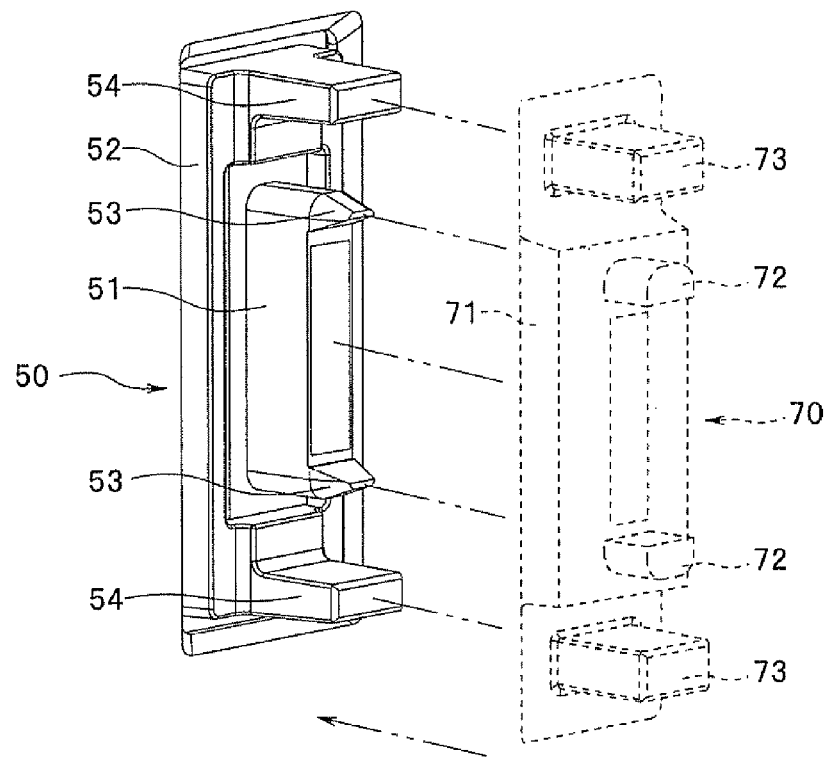
FIG. 9 is a figure schematically showing a state before an electric connector of the connector box is connected to an electric connector of the connector box housing chamber.
Figure 10:
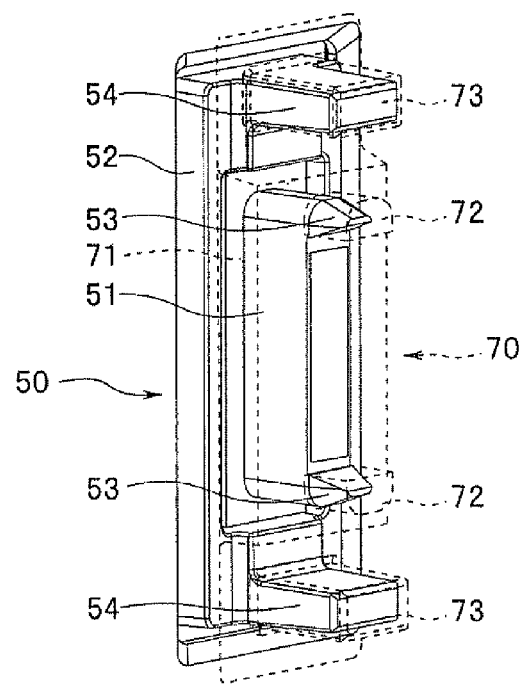
FIG. 10 is a figure schematically showing a state where the electric connector of the connector box is connected to the electric connector of the connector box housing chamber of FIG. 9.

FIG. 9 is a figure schematically showing a state before an electric connector of the connector box is connected to an electric connector of the connector box housing chamber. FIG. 10 is a figure schematically showing a state where the electric connector of the connector box is connected to the electric connector of the connector box housing chamber of FIG. 9.

As shown in FIG. 1, a main part of an endoscope apparatus 1 is configured by an endoscope 2, and an apparatus main body 3 to which the endoscope 2 is connected.

A main part of the endoscope 2 is configured by a thin and long insertion portion 20 having flexibility, an operation portion 21 connected to the insertion direction proximal end side of the insertion portion 20, a universal cord 22 which is a flexible connection cable extended from the operation portion 21, and a connector box 40 (see FIG. 2 and FIG. 3) which is a connector main body, as will be described below, connected to the extended end of the universal cord 22. The endoscope 2 and the apparatus main body 3 are connected to each other by the connector box 40.

In the inside of the distal end portion of the insertion portion 20, there are arranged an objective optical system having an objective lens or the like, an image pickup unit having an image pickup device, such as a CCD, for picking up an image of a part to be tested, a light source, such as an LED, for illuminating the part to be tested, and the like (all not shown).

The image pickup unit or the light source may be provided in the inside of the operation portion 21, or in a closed space 200, as will be described below (see FIG. 11), which is closed by an exterior housing 4 of the apparatus main body 3 and exterior housings 30 and 31 of the connector box 40.

The apparatus main body 3 has, for example, a box shape, and the exterior housing 4 of the apparatus main body 3 is formed of a hard metal, such as magnesium, which is a heat conducting member for radiating the heat in the atmosphere in the closed space 200, as will be described below, to the outside of the exterior housing 4.

Further, a monitor 5 which has an image display portion 8, such as an LCD (Liquid Crystal Display), for displaying an endoscopic image picked up by the image pickup unit of the endoscope 2, is fixed to the exterior housing 4.

Particularly, the monitor 5 is fixed to the outer surface of the apparatus main body 3 via a rotary supporting portion 13 (see FIG. 2). A stay (not shown) is provided in the rotary supporting portion 13, and the monitor 5 is rotatably held by the stay.

More particularly, the stay is connected to the monitor 5, and whereby a frame body of the monitor 5, in which an image display portion 8 is provided and which is formed of, for example, a synthetic resin, is rotatably held by the stay. An image signal subjected to photoelectric conversion by the image pickup unit of the endoscope 2, is outputted to the monitor 5 by a communication cable 18 extended from the apparatus main body 3.

Further, when the endoscope apparatus 1 is used, the monitor 5 is used in a raised state where a rear face portion 7 on the opposite side of a monitor face 6 on which the image display portion 8 is formed, is rotated in a direction away from the connector box 40, as will be described below (see FIG. 2 and FIG. 3), which is mounted to a rear face side of the exterior housing 4 of the apparatus main body 3 as shown in FIG. 1. When the endoscope apparatus 1 is not used, the monitor 5 is closed in such a manner that the rear face portion 7 of the monitor 5 is rotated so as to be in contact with the connector box 40.

When the endoscope apparatus 1 is not used, a cover plate 9 which covers and protects the image display portion 8 is fixed to the monitor face 6 of the monitor 5. The cover plate 9 is fixed to the monitor face 6 in such a manner that an opposite face 10 of the cover plate 9, which faces the image display portion 8, is freely opened and closed with respect to the image display portion 8.

Further, a plurality of legs 29 formed of rubber, such as NBR for placing the apparatus main body 3, are fixed to corners of the exterior housing 4 of the box shaped apparatus main body 3. The legs 29 are provided in the apparatus main body 3 so that the apparatus main body 3 can be placed in a plurality of postures with respect to a ground surface, and the like.

As shown in FIG. 4, a concave connector box housing chamber 45 (hereinafter referred to simply as a housing chamber), to which the connector box 40 is mounted, is provided on an outer surface 11 side of a rear side of the exterior housing 4 of the apparatus main body 3. The connector box housing chamber 45 is formed to have substantially the same planar shape as the outer shape of the connector box 40.

In the housing chamber 45, a plurality of slits 44 are formed, as shown in FIG. 5, at positions which respectively face a plurality of slits 63 (see FIG. 6) formed in the connector box 40, as will be described below, at the time when the connector box 40 is mounted to the housing chamber 45 as shown in FIG. 8.

When the connector box 40 is mounted to the housing chamber 45 as shown in FIG. 8, the plurality of slits 44 communicate with the plurality of the slits 63, so that one closed space 200 (see FIG. 11) is configured by a space 200a (see FIG. 11) in the exterior housing 4 of the apparatus main body 3 and a space 200b (see FIG. 11) in the exterior housing configured by the frame member 30 and the lid 31 of the connector box 40, as will be described below (see FIG. 3).

Further, as shown in FIG. 5, there is provided in the housing chamber 45 a convex electric connector 50, or the like, which, when the connector box 40 is mounted to the housing chamber 45, is electrically connected to a concave female connector 70 (see FIG. 6) which is an electric connector of the connector box 40.

Further, as shown in FIG. 4, the exterior housing 4 is provided with a handle portion 17 for handling at one side portion (top side seen toward the paper surface), and the above described stay provided in the rotary supporting portion 13 for rotatably holding the monitor 5 is fixed to the one side portion.

Further, in the exterior housing 4, as shown in FIG. 2, two shock absorbing portions 14 and 15 for the monitor, projecting from the side in which the housing chamber 45 is provided, are formed integrally with the exterior housing 4.

The shock absorbing portions 14 and 15 for the monitor are members for preventing the monitor 5 from being brought into contact with the exterior housing 4, in the state where the monitor 5 is rotatably closed in contact with the connector box 40.

Further, the shock absorbing portions 14 and 15 for the monitor prevent that, when a shock is applied to the apparatus main body 3, the apparatus main body 3 is brought into contact with the monitor 5 to thereby cause the monitor 5 to drop out of the apparatus main body 3. Further, a recessed portion 16, into which the universal cord 22 of the endoscope 2 is inserted and arranged, is formed in the shock absorbing portion 15 for the monitor.

As shown in FIG. 3, the connector box 40 of the endoscope 2 is a substantially box shaped member fixed to a connector 23 provided at the extended end of the universal cord 22. The main part of the connector box 40 is configured by the concave frame member 30 configuring an exterior housing, and the thin plate shaped lid 31 by which the exterior housing is configured so as to be freely opened and closed with respect to the opening of the frame member 30.

Further, the frame member 30 and the lid 31 are formed of a hard metal, such as magnesium, which is a heat conducting member for radiating heat in the atmosphere in the closed space 200 (see FIG. 11) to the outside of the frame member 30 and the lid 31.

Here, as shown in FIG. 3, two shock absorbing members 39 are provided on the surface of the lid 31. The shock absorbing members 39 have a substantially columnar shape, and are formed of an elastic member, such as rubber.

The shock absorbing member 39 is configured such that a contact surface 39a thereof is brought into contact with the rear face portion 7 of the monitor 5 in the state where the monitor 5 is stored in the apparatus main body 3 during the time when the endoscope apparatus 1 is not used. That is, the shock absorbing member 39 is provided so as to absorb various shocks which are applied to the monitor 5 during the time when the monitor 5 is stored in the apparatus main body 3.

Further, the lid 31 is configured so as to be freely opened and closed with respect to the frame member 30 by a plurality of screws 38. Further, CCU substrates 170a and 170b for controlling the image pickup unit, as will be described below (see FIG. 11), and the like, are provided in the space 200b (see FIG. 1) in the connector box 40. The detailed configuration of the connector box 40 will be described below.

Returning to FIG. 1, in the apparatus main body 3, as will be described below, there are provided a power source substrate 165 (see FIG. 11), a main substrate 160 (see FIG. 11) electrically connected to a CPU 161 for image processing (see FIG. 11), a fan 180 (see FIG. 11), a recording medium which records image data subjected to image processing, a battery which supplies electric power to the endoscope 2 and the apparatus main body 3, and the like. The detailed configuration of the apparatus main body 3 will also be described below.

It is configured such that the battery is freely inserted and extracted to and from a battery housing chamber 210 (see FIG. 11) in the apparatus main body 3 as will be described below, by opening and closing of a lid 27 for the battery, which is provided so as to be freely opened and closed with respect to the side surface of the exterior housing 4 by a hinge 28. Further, after the battery is inserted and housed in the battery housing chamber 210, the lid 27 for the battery is locked by a fixing pin 26.

Next, a configuration for enabling the apparatus main body 3 and the connector box 40 to be detachably mounted to each other, will be described with reference to FIG. 4 to FIG. 6. The monitor 5 is not shown in FIG. 4.

In the housing chamber 45 of the apparatus main body 3, as shown in FIG. 4, a connector connection recessed portion 46 is formed so as to be further recessed from the bottom surface which is a surface in contact with the connector box 40, toward the surface side of the apparatus main body 3.

Further, in the housing chamber 45, as shown in FIG. 5, there are provided side by side two long shock absorbing portions 47 which are formed of an elastic member, or the like, and which absorbs a shock caused by the contact with the contact surface of the connector box 40.

Two engagement projecting portions 48 are formed in a rail shape along the opening direction, at both side surface portions located on each of the upper side and the lower side of the connector connection recessed portion 46, so as to sandwich the plurality of slits 44. Surface circular shaped recessed portions 49 are formed at four corners (only two are shown in FIG. 5) of the bottom surface of the connector connection recessed portion 46.

The electric connector 50 is provided substantially at the center of the bottom surface of the connector connection recessed portion 46, and two shock absorbing portions 55 are provided so as to sandwich the electric connector 50. The shock absorbing portions 55 have the same configuration as that of the above described shock absorbing portion 47, and are provided in order to absorb a shock caused by the contact with the contact surface of the connector box 40.

The electric connector 50 is configured by a male connector 51 and a connector frame 52 arranged so as to surround the male connector 51. The male connector 51 has projecting portions 53 respectively at the both longitudinal ends thereof, which project in the opening direction of the connector connection recessed portion 46.

Further, the connector frame 52 also has guiding projecting portions 54 which configure, respectively at the both longitudinal ends of the connector frame 52, portions to be guided projecting in the opening direction of the connector connection recessed portion 46. The guiding projecting portion 54 projects more in the opening direction of the connector connection recessed portion 46 than the projecting portion 53. That is, the projecting amount of the guiding projecting portion 54 from the bottom surface of connector connection recessed portion 46 is larger than that of the male connector 51.

Further, as shown in FIG. 6, the connector box 40 has a housing connecting portion 61 having substantially the same shape as that of the housing chamber 45 of the apparatus main body 3, on the side which is mounted to the housing chamber 45. The housing connecting portion 61 has a connector connection projecting portion 62 which projects from the surface of the housing connecting portion 61 so as to have substantially the same shape as that of the connector connection recessed portion 46.

Further, in the housing connecting portion 61, there are formed the plurality of slits 63, which communicate with the plurality of slits 44 in the housing chamber 45 in the state where the connector box 40 is mounted to the housing chamber 45 as shown in FIG. 8.

In the connector connection projecting portion 62, there are formed four guide grooves 64 in which the engagement projecting portions 48 of the connector connection recessed portion 46 are engaged in the state where the connector box 40 is mounted to the housing chamber 45 as shown in FIG. 8.

Further, in the connector connection projecting portion 62, there are formed disc-like shock absorbing members 65, which are formed of an elastic member and which are engaged with the recessed portions 49 of the connector connection recessed portion 46 in the state where the connector box 40 is mounted to the housing chamber 45 as shown in FIG. 8.

Further, in the connector connection projecting portion 62, there is provided the female connector 70 which is connected to the electric connector 50 as shown in FIG. 10 in the state where the connector box 40 is mounted to the housing chamber 45 as shown in FIG. 8.

The female connector 70 has a recessed portion 71 in which the male connector 51 formed in the connector connection projecting portion 62 is engaged as shown in FIG. 10 in the state where the connector box 40 is mounted to the housing chamber 45 as shown in FIG. 8.

In the female connector 70, there are provided engaging holes 72 in which the projecting portions 53 of the male connector 51 are engaged as shown in FIG. 10 in the state where the connector box 40 is mounted to the housing chamber 45 as shown in FIG. 8, and guiding engagement holes 73 which are holes for guiding and engaging the guiding projecting portions 54 of the connector frame 52 of the male connector 51.

When the connector box 40 configured as described above is mounted in the housing chamber 45 in a manner as shown in FIG. 7 and FIG. 8, claw portions 42 of two rotation fasteners 41, which are provided on the exterior housing 4, are locked with two locking portions 37 of the connector box 40 so as to make the state as shown in FIG. 2, and thereby the connector box 40 is fixed and housed in the housing chamber 45.

When mounting the connector box 40 to the apparatus main body 3, the user is able to easily recognize the mounting direction by adjusting the connector connection projecting portion 62 of the connector box 40 to the connector connection recessed portion 46 of the housing chamber 45 as shown in FIG. 7 and FIG. 8. Thereby, it is possible to prevent erroneous mounting of the connector box 40 by a user.

Further, the female connector 70 of the electric connector 50 on the side of the connector box 40 is connected to the male connector 51 of the housing chamber 45 so that the state of the female connector 70 and the male connector 50 shown in FIG. 10 is changed from the state thereof shown in FIG. 9.

That is, the guiding projecting portions 54 projecting from the connector frame 52 of the male connector 51 are first guided and engaged in the guiding engagement holes 73 on the side of the female connector 70, and the male connector 51 and the female connector 70 face each other so as to be set in predetermined connecting positions.

Then, the projecting portions 53 of the male connector 51 are accurately engaged in the engaging holes 72 on the side of the female connector 70, so that the male connector 51 and the female connector 70 are electrically connected to each other in the state as shown in FIG. 10.

Further, even when the connector box 40 is mounted by the user to the housing chamber 45 of the exterior housing 4 of the apparatus main body 3, for example, in an oblique direction which is not the normal mounting direction, the connector connection recessed portion 46 is securely brought into contact with the connector connection projecting portion 62 of the connector box 40, since the guiding projecting portion 54 is more projected to the opening direction of the connector connection recessed portion 46 than the projecting portion 53.

As a result, the contact between the male connector 51 and the connector connection projecting portion 62 is prevented by the guiding projecting portion 54. Thus, an excessive load is not applied to the male connector 51, and thereby the breakage of the male connector 51 is prevented.

Next, a configuration in the inside of the apparatus main body 3 and the connector box 40 will be described with reference to FIG. 11 to FIG. 13.

Figure 11:
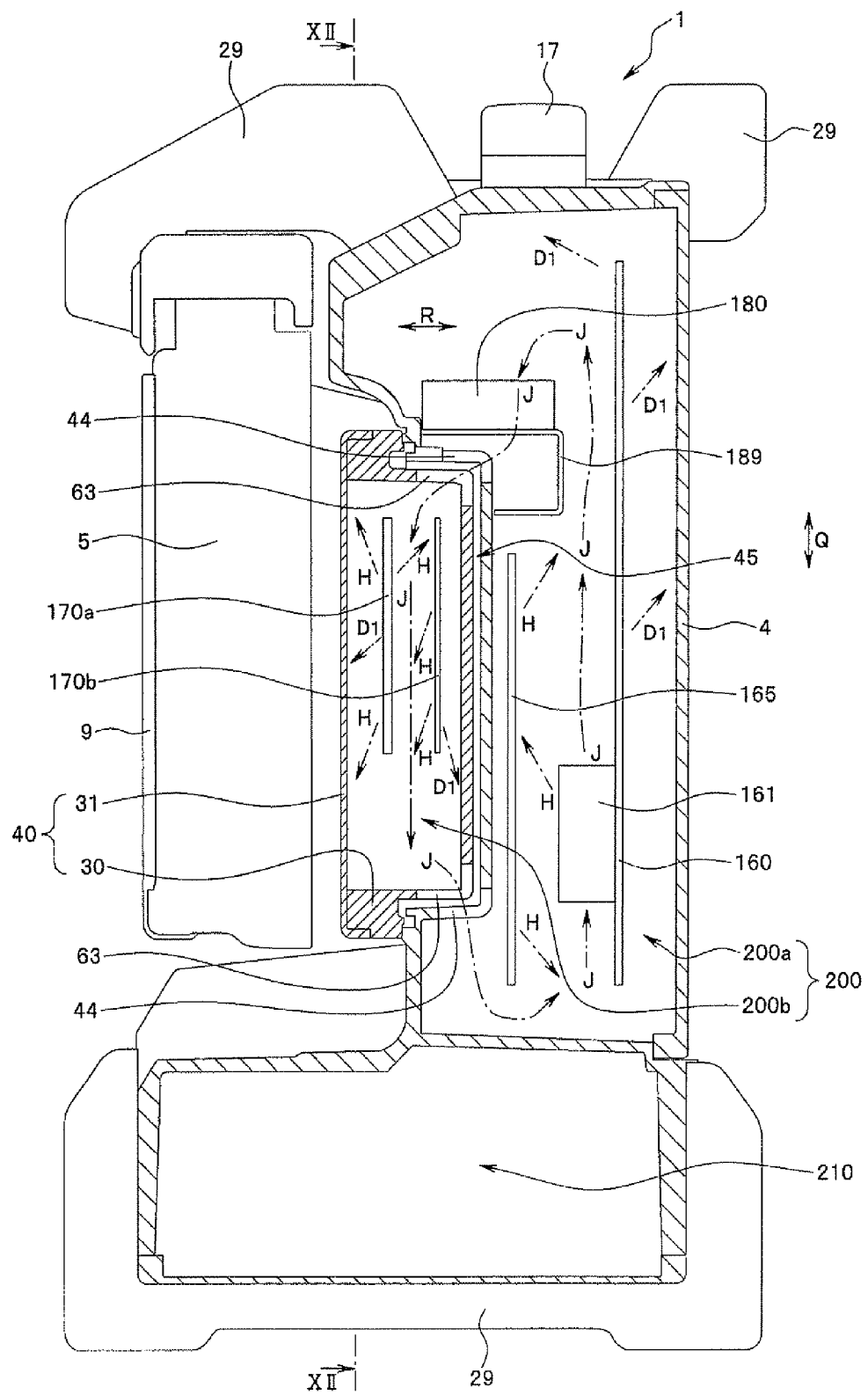
FIG. 11 is a partial sectional view of the endoscope apparatus in a state where the connector box is mounted to the housing chamber of the apparatus main body.

FIG. 11 is a partial sectional view of the endoscope apparatus in the state where the connector box is mounted to the housing chamber of the apparatus main body. FIG. 12 is a partial sectional view of the endoscope apparatus along the line XII-XII in FIG. 11.

As shown in FIG. 11, in the inside of the apparatus main body 3, the battery housing chamber 210 capable of freely housing a battery which supplies electric power to the above described apparatus main body 3 and the light source via an illumination cable, is formed in the lower portion in a height direction Q when the handle portion 17 of the endoscope apparatus 1 is set as the upper side.

Further, in the state where the connector box 40 is mounted to the housing chamber 45 of the apparatus main body 3 as shown in FIG. 8, the slit 44 of the housing chamber 45 communicates with the slit 63 of the connector box 40, so that as shown in FIG. 11, the one closed space 200 is formed above the battery housing chamber 210 in the height direction Q, in the inside closed by the exterior housing 4 of the apparatus main body 3 and the inside closed by the frame member 30 and the lid 31 of the connector box 40. The closed space 200 is configured by the space 200a in the apparatus main body 3 and the space 200b in the connector box 40.

In the space 200a of the closed space 200, the main substrate 160, such as a CPU video board on which a plurality of electrical components such as the CPU 161 for image processing are fixed, and the power source substrate 165 are provided along the height direction Q and in parallel with each other in the arrangement direction R perpendicular to the height direction Q.

In FIG. 11, for the sake of simplicity, it is shown that only the CPU 161 for image processing is fixed on the main substrate 160. However, in practice, an electrical component which controls the light quantity of the light source, an electrical component which controls the drive of the fan 180 as will be described below, and the like, are also fixed on the main substrate 160. Further, the CPU 161 for image processing is adapted to process, for example, a subject image signal outputted from the image pickup unit.

Further, the main substrate 160, the power source substrate 165, and the CPU 161 are heat generating portions which generate heat by being driven.

When the connector box 40 is mounted to the housing chamber 45 of the apparatus main body 3, in the inside of the connector box 40, as shown in FIG. 11, the two CCU substrates 170a and 170b for controlling the image pickup unit are provided side by side in parallel with the main substrate 160 and the power source substrate 165 in the arrangement direction R along the height direction Q. The CCU substrates 170a and 170b are heat generating portions which generate heat by being driven.

Further, in the space 200a, a fan supporting member 189 is fixed to the exterior housing 4 at a position opposite the slit 44. On the upper face of the fan supporting member 189 in the height direction Q, for example, two fans 180 configuring heat dissipating means and a heat diffusion member, which perform at least one of dissipation of heat of the above described heat generating portion to the atmosphere in the closed space 200, or transfer of heat in the atmosphere in the closed space 200 to the exterior housing 4, the frame member 30, and the lid 31, are provided in the direction perpendicular to the height direction Q and the arrangement direction R as shown in FIG. 12. The fan 180 also has a function to generate convection J in the closed space 200. Further, the fan 180 is configured by a small axial fan.

Further, when the connector box 40 is mounted to the housing chamber 45 of the apparatus main body 3 as shown in FIG. 11, the fan 180 is fixed to the fan supporting member 189 so as to overlap with the CCU substrate 170b and the power source substrate 165 in the arrangement direction R in a plane view from the above in the height direction Q, that is, so as to stride over the CCU substrate 170b and the power source substrate 165 in the arrangement direction R. Thereby, the width of the space 200a in the arrangement direction R, in which space the fan 180 is arranged, can be reduced, so that it is possible to reduce the thickness of the apparatus main body 3.

As shown in FIG. 11, a space (not shown) is formed in the face of the fan supporting member 189, on which face the fan 180 is provided, and thereby the inside of the fan supporting member 189 communicates with the slit 44, so that the fan 180 communicates with the slit 44 through the space of the fan supporting member 189.

Next, the effects of the present embodiment configured in this way will be described with reference to FIG. 11, FIG. 12 and FIG. 13. FIG. 13 is a figure schematically showing the heat transfer to the exterior housing, the heat conduction in the exterior housing, and the heat radiation from the exterior housing to the outside.

First, when the connector box 40 is mounted to the housing chamber 45 of the apparatus main body 3 as shown in FIG. 8, the slit 44 of the housing chamber 45 communicates with the slit 63 of the connector box 40, as described above, and thereby the closed space 200, which is closed by the exterior housing 4, the frame member 30, and the lid 31, is formed in the inside of the exterior housing 4, the frame member 30, and the lid 31.

Thereafter, when the CCU substrates 170a and 170b, the main substrate 160, the CPU 161, and the power source substrate 165 (hereinafter collectively referred to as a heat generating portion) are driven by the driving of the endoscope 2 or the like, the heat generating portion generates heat, so that the atmosphere in the closed space 200 is heated.

At this time, when the two fans 180 are driven to start air supply, the wind of the air supplied from the each fan 180 enters into the space 200b in the connector box 40 through the fan supporting member 189, and through the slit 44 and the slit 63 which are provided in the upper portion of the connector box 40 in the height direction Q, as shown in FIG. 11. Then, the wind enters into the space 200a in the apparatus main body 3 through the slit 44 and slit 63, which are provided in the lower portion of the connector box 40 in the height direction Q. And the wind is again sucked by the each fan 180, so that the convection J is generated.

The heat of the heat generating portion is actively dissipated by the convection J to the closed space 200. In other words, a heat dissipation flow H is generated from the heat generating portion, so that the heat generating portion is cooled by the generation of the active heat dissipation flow H.

Further, the heat in the heated atmosphere in the closed space 200 is actively transferred to the exterior housing 4, the frame member 30, and the lid 31 by the convection J. That is, a heat transfer flow D1 is generated in the whole closed space 200.

The heat in the atmosphere of the space 200a is not only transferred by the heat transfer flow D1 to the exterior housing 4, but also is moved to the space 200b, so as to be transferred to the frame member 30 and the lid 31. Further, the heat in the atmosphere of the space 200b is not only transferred to the frame member 30 and the lid 31, but also is moved into the space 200a, so as to be transferred to the exterior housing 4.

Figure 13:
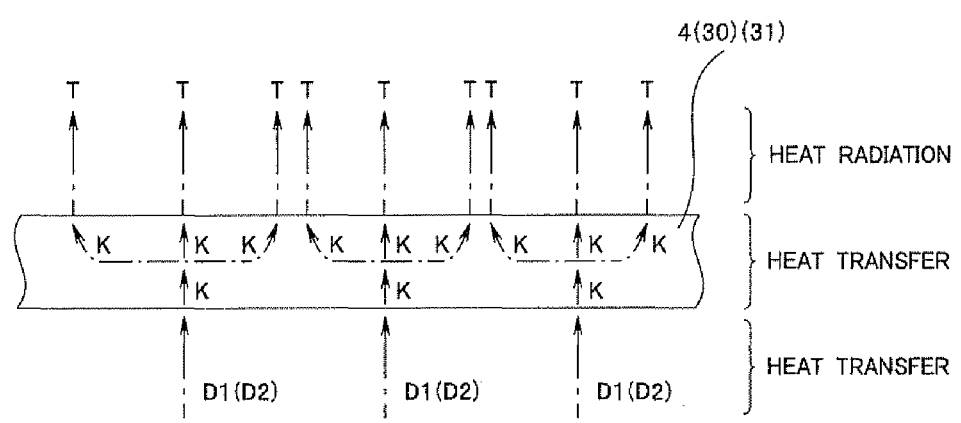
FIG. 13 is a figure schematically showing the heat transfer to an exterior housing, the heat conduction therein, and the heat radiation therefrom to the outside.

As a result, since the exterior housing 4, the frame member 30, and the lid 31 are configured by a member, such as magnesium, having a high thermal conductivity, the heat in the atmosphere in the closed space 200 transferred to the exterior housing 4, the frame member 30, and the lid 31 is conducted, as shown in FIG. 13. The heat is conducted from the inside of each of the exterior housing 4, the frame member 30, and the lid 31 to the outside thereof where the temperature is lower than that of the closed space 200, over a wide range of the exterior housing 4, the frame member 30, and the lid 31. That is, as shown in FIG. 13, a heat conduction flow K is generated in the exterior housing 4, the frame member 30, and the lid 31.

Finally, the heat in the atmosphere in the closed space 200 is radiated from the outer surface of the exterior housing 4, the frame member 30, and the lid 31 to the outside of the exterior housing 4, the frame member 30, and the lid 31.

That is, as shown in FIG. 13, a heat radiation flow T is generated from the outer surface of the exterior housing 4, the frame member 30, and the lid 31. The ground surface on which the apparatus main body 3 is placed is also included in the outside of the exterior housing 4, the frame member 30, and the lid 31.

Thereby, the heat in the atmosphere in the closed space 200 is discharged to the outside of the exterior housing 4, the frame member 30, and the lid 31 by the fans 180, so that the atmosphere in the closed space 200 is cooled.

As described above, in the present embodiment, it is described that when the connector box 40 is mounted to the housing chamber 45 of the apparatus main body 3, the slit 44 communicates with the slit 63, so as to thereby form a closed space 200 in the inside of the exterior housing 4, the frame member 30, and the lid 31, and that the fans 180 are also provided in the closed space 200. Further, it is described that the fans 180 generate the convection J in the closed space 200, and perform at least one of dissipation of the heat of the heat generating portion to the closed space 200, and transfer of the heat in the atmosphere in the closed space 200 to the exterior housing 4, the frame member 30, and the lid 31.

Further, it is described that by using the convection J, the heat of the heat generating portion is actively dissipated to the closed space 200, and then the heat in the atmosphere in the closed space 200 is actively transferred to the exterior housing 4, the frame member 30, and the lid 31.

It is described that the heat in the heated atmosphere in the closed space 200 is then radiated from the outer surface of the exterior housing 4, the frame member 30, and the lid 31 through the heat conduction in the exterior housing 4, the frame member 30, and the lid 31.

Thereby, the heat of the heat generating portion is efficiently and securely cooled by the air supplied by the fans 180, and the heat in the atmosphere in the closed space 200 is radiated to the outside of the exterior housing 4, the frame member 30, and the lid 31, so that the heated atmosphere in the closed space 200 is cooled.

Therefore, even when the heat generating portion which generates heat is arranged in the closed space 200 closed by the exterior housing 4, the frame member 30, and the lid 31, it is possible to efficiently and securely prevent excessive heating of the atmosphere in the closed space 200, and troubles, such as degradation of reliability, of the heat generating portion due to the excessive heating.

Further, the heat generating portion is arranged in the closed space 200 closed by the exterior housing 4, the frame member 30, and the lid 31, and thereby it is possible to prevent raindrops from entering into the closed space 200 in a rainy weather, and to prevent that foreign matters, such as dust, entering into the closed space 200, so as not to cause a trouble in the heat generating portion. This makes it possible to use the endoscope apparatus 1 outdoors.

Modifications of the embodiment described above will be described below.

In the present embodiment, it is described that the two fans 180 are provided on the fan supporting member 189, however, it is needless to say that two or more fans 180 may be provided. Further, the fan 180 may be periodically, reversely rotated, or the head thereof may be oscillated to thoroughly generate the convection J in the atmosphere in the closed space 200.

Figure 12:
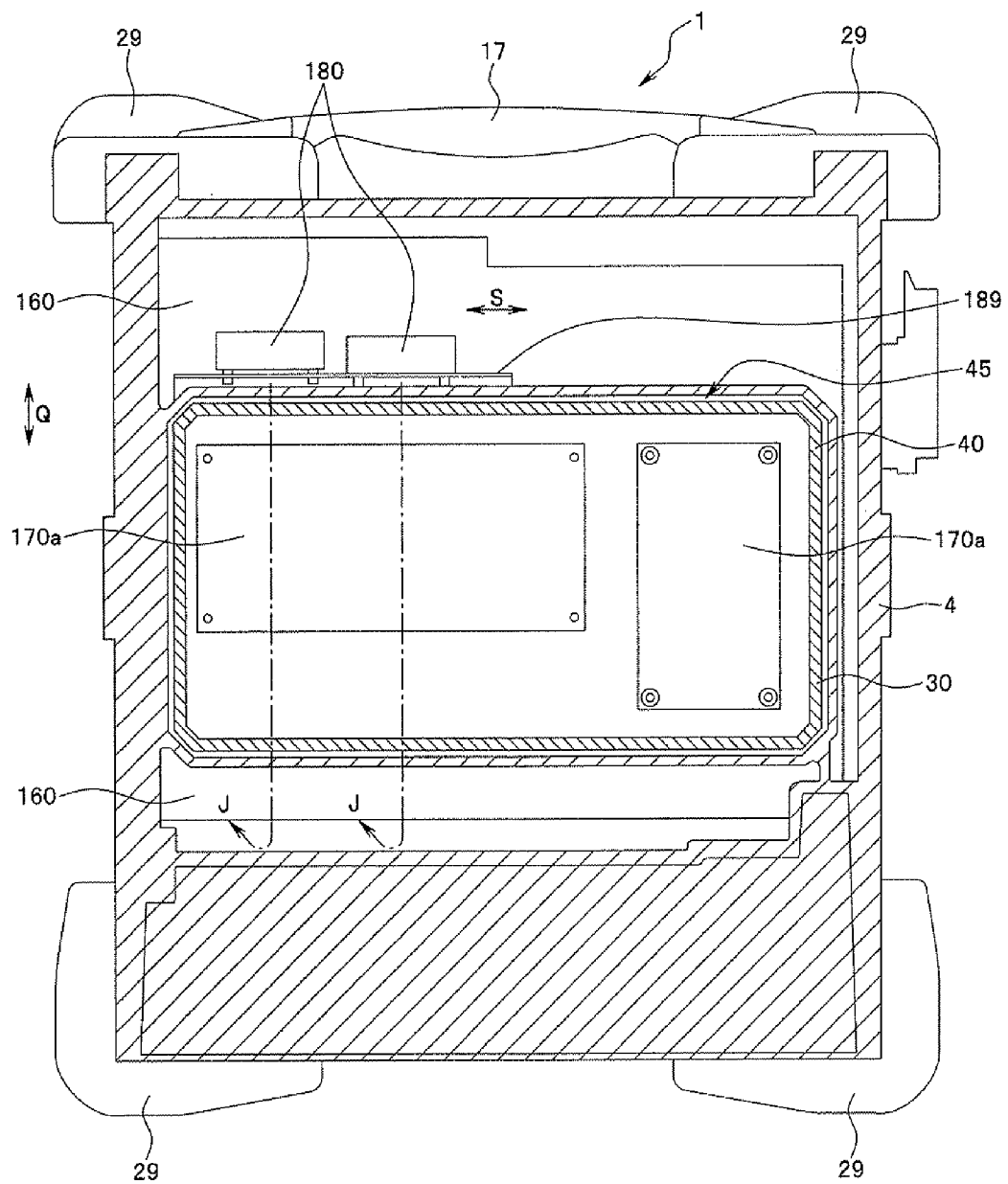
FIG. 12 is a partial sectional view of the endoscope apparatus along the line XII-XII in FIG. 1.

Further, the arrangement position of the fan 180 is not limited to the above described positions as shown in FIG. 11 and FIG. 12, but the fan may be arranged at any position where the convention J can be thoroughly generated in the atmosphere in the closed space 200, and the heat generating portion can be securely cooled.

Specifically, the fan 180 may be provided near the exterior housing 4 with opposed thereto, and may be configured such that the frame member 30, and the lid 31, and locally supplies air to the exterior housing 4, the frame member 30, and the lid 31, which face the fan 180, so as to thereby make the heat in the heated atmosphere in the closed space 200 locally and actively transferred to the exterior housing 4, the frame member 30, and the lid 31 which face the fan 180. Thereby, the atmosphere in the closed space 200 is more efficiently cooled.

Also in this case, the heat of the atmosphere in the closed space 200, which is transferred to the exterior housing 4, the frame member 30, and the lid 31 which face the fan 180, is radiated to the outside of the exterior housing 4, the frame member 30, and the lid 31 from the outer surface of the exterior housing 4, the frame member 30, and the lid 31, through the heat transfer in the exterior housing 4, the frame member 30, and the lid 31, as described above.

Further, it may also be configured such that the fan 180 is provided at a position opposing the heat generating portion, and locally supplies air to the heat generating portion, so as to thereby make the heat of the heat generating portion locally dissipated to the closed space 200.

Further, in the present embodiment, it is described that the fan 180 is provided in the space 200a of the apparatus main body 3 in the closed space 200, but the fan 180 may also be provided in the space 200b in the connector box 40.

Further, in the present embodiment, it is described that the heat generating portion is described by taking, as examples, electrical components such as the CCU substrates 170a and 170b, the main substrate 160, the CPU 161, and the power source substrate 165, but the present invention is not limited to these. It is needless to say that the present invention may be applied to any component, that is arranged in the closed space 200 and generates heat by the driving of the endoscope 2.

Second Embodiment

Figure 14:
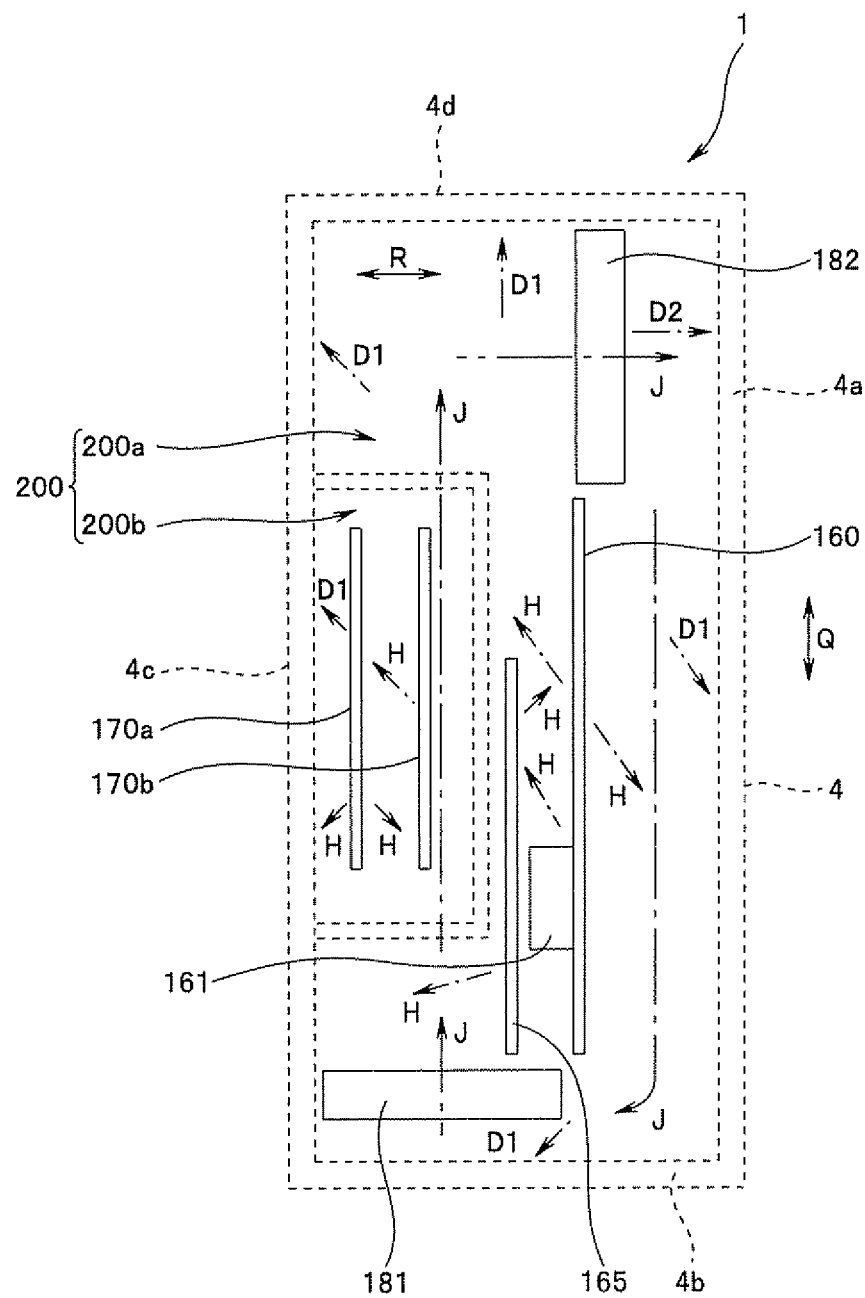
FIG. 14 is a figure schematically showing the inside of an endoscope apparatus according to a second embodiment.

FIG. 14 is a figure schematically showing the inside of an endoscope apparatus according to a second embodiment.

The configuration of the endoscope apparatus according to the second embodiment is different from the above described endoscope apparatus 1 shown in FIG. 1 to FIG. 13, only in that a plurality of fans are arranged in the closed space 200, and are respectively arranged in different positions. In the following, only the different points are described. Thus, the same parts and components as those in the first embodiment are denoted by the same reference numerals and characters, and the explanation of thereof is omitted.

In the closed space 200, fans 181 and 182 configuring heat dissipation means and a heat diffusion member, which by convecting the atmosphere in the closed space 200 by air supply, effect one of dissipation of the heat of the heat generating portion to the closed space 200, and transfer of the heat in the atmosphere in the closed space 200 to the exterior housing 4, the frame member 30, and the lid 31, are arranged in such a manner that the air supply directions of the fans 181 and 182 are different from each other.

The fans 181 and 182 also have a function to generate convention J in the closed space 200. Further, the fans 181 and 182 are configured by a small axial fan. Further, the fan 181 and fan 182 may have a different air volume, respectively.

As shown in FIG. 14, the fan 182 is arranged above the main substrate 160 in the height direction Q and adjacent one face 4a and one face 4d of the exterior housing 4, so that the air supply direction of the fan 182 faces the one face 4a.

The fan 182 locally and actively transfers the heat in the atmosphere in the closed space 200 heated by the heat dissipated from the heat generating portion to the adjacent one face 4a by locally supplying air to the adjacent one face 4a.

The fan 181 is arranged adjacent and below the main substrate 160 in the height direction Q and arranged adjacent one face 4b and one face 4c so that the air supply direction of the fan 181 is faces the one face 4d via the closed space 200.

By supplying air to the closed space 200 from one end to the other end of the exterior housing 4, specifically, from the one face 4b to the one face 4d, the fan 181 actively dissipates the heat of the heat generating portion to the closed space 200, and actively transfers the heat in the atmosphere in the closed space 200, which is heated by the active heat dissipation, the driving of the heat generating portion, and the like, to a part of the exterior housing 4, the frame member 30, and the lid 31, for example, to the one face 4d and the one face 4c.

Further, in the state where the fan 181 is arranged in the closed space 200 together with the fan 182, the fan 181 supplies air together with the fan 182, and thereby generates, specifically, the convection J in the whole closed space 200 as shown in FIG. 14, so as to actively dissipate the heat of the heat generating portion to the closed space 200, and to actively transfer the heat in the heated atmosphere in the closed space 200 to the exterior housing 4, the frame member 30, and the lid 31.

In this way, in the present embodiment, the fans 181 and 182 are arranged in the different positions in the closed space 200. Thus, in the present embodiment, an electrical component which controls the light quantity of the light source, an electrical component which controls the driving of the fans 180 and 181, and the like, are fixed on the main substrate 160 in addition to the CPU 161 for image processing.

Next, the effects of the present embodiment configured in this way will be described.

First, when the connector box 40 is mounted to the housing chamber 45 of the apparatus main body 3 as shown in FIG. 8, the slit 44 of the housing chamber 45 communicates with the slit 63 of the connector box 40 as described above, and thereby the closed space 200 closed by the exterior housing 4, the frame member 30, and the lid 31 is formed in the inside of the exterior housing 4, the frame member 30, and the lid 31.

Thereafter, when the heat generating portion is driven by the driving or the like of the endoscope 2, the heat generating portion generates heat, so that the atmosphere in the closed space 200 is heated.

At this time, when the fan 182 and the fan 181 are driven, that is, the respective fans start air supply, the wind of air supplied by the fan 182 is sucked by the fan 181, and the wind of air supplied by the fan 181 is sucked by the fan 182, since the fan 182 and the fan 181 are arranged in the closed space 200 so that the air supply directions of the fans are different from each other as described above. As a result, the convection J is thoroughly generated in the atmosphere in the closed space 200.

The heat of the heat generating portion is actively dissipated by the convection J to the closed space 200. In other words, a heat dissipation flow H is generated from the heat generating portion, so that the heat generating portion is cooled by the generation of the active heat dissipation flow H.

Further, the heat in the heated atmosphere in the closed space 200 is actively transferred to the exterior housing 4, the frame member 30, and the lid 31 by the convection J. That is, a heat transfer flow D1 is thoroughly generated in the closed space 200. The other effects and the heat flow from the closed space 200 to the outside of the exterior housing 4, the frame member 30, and the lid 31 are the same as those of the first embodiment as described in FIG. 13, and hence the explanation thereof is omitted.

Further, as the other effect different from those of the first embodiment, the fan 182 locally and actively transfers the heat in the heated atmosphere in the closed space 200 to the adjacent one face 4a by locally supplying air to the adjacent one face 4a, that is, the atmosphere in the closed space 200 is more efficiently cooled by the generation of a local heat transfer flow D2.

Also in this case, the heat of the atmosphere in the closed space 200 transferred to the one face 4a is radiated to the outside of the exterior housing 4, the frame member 30, and the lid 31 from the outer surface of the one face 4a through the heat transfer in the one face 4a, as described above.

In this way, in the present embodiment, the fans 182 and 181 are arranged in the closed space 200 closed by the exterior housing 4, the frame member 30, and the lid 31 so as to make the air supply directions of the fans 182 and 181 different from each other, and thereby the convection J is generated by the air supplied by the fans 182 and 181.

Further, the heat of the heat generating portion is actively dissipated to the closed space 200 by using the convection J. Then, the heat in the heated atmosphere in the closed space 200 is actively transferred to the exterior housing 4, the frame member 30, and the lid 31. Further, the heat in the heated atmosphere in the closed space 200 is locally and actively transferred to the one face 4a by using the fan 182. Thereafter, the heat in the heated atmosphere in the closed space 200 is radiated from the outer surface of the exterior housing 4, the frame member 30, and the lid 31 through the heat conduction in the exterior housing 4, frame member 30, and lid 31.

Thereby, the heat of the heat generating portion is efficiently and securely cooled by the air supply of the fans 182 and 181, and the heat in the atmosphere in the closed space 200 is radiated to the outside of the exterior housing 4, the frame member 30, and the lid 31. As a result, the heated atmosphere in the closed space 200 is cooled.

From the above, it is possible to obtain the same effects as those of the above described first embodiment.

Modifications will be described below.

In the present embodiment, the two fans 182 and 181 are provided in the closed space 200, but the present invention is not limited thereto. It is needless to say that two or more fans may also be arranged.

Further, the arrangement positions of the fans 182 and 181 are not limited to the positions as described above described with reference to FIG. 14. The fans may be arranged in any positions, where the convection J can be thoroughly generated in the atmosphere in the closed space 200, and enable the heat generating portion to be securely cooled.

Further, the present embodiment is also described by taking, as an example of the heat generating portion, the electrical components, such as the CCU substrates 170a and 170b, the main substrate 160, the CPU 161, and the power source substrate 165, but the present invention is not limited thereto. The present invention may be applied to any component, that is arranged in the closed space 200 and generates heat by the driving of the endoscope 2.

Third Embodiment

Figure 15:
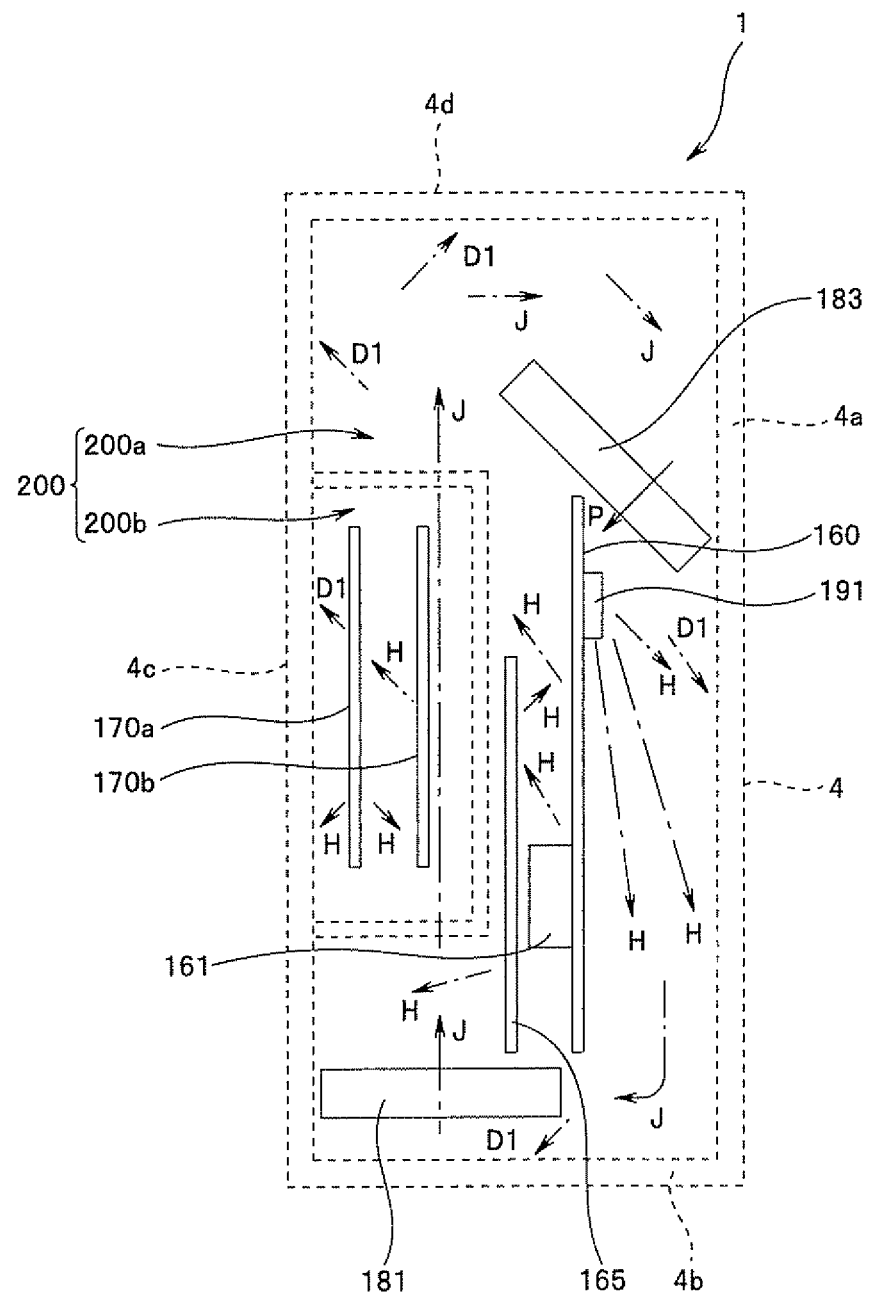
FIG. 15 is a figure schematically showing the inside of an endoscope apparatus according to a third embodiment.

FIG. 15 is a figure schematically showing the inside of an endoscope apparatus according to a third embodiment.

The configuration of the endoscope apparatus according to the third embodiment is different from that of the endoscope apparatus according to the second embodiment as shown in FIG. 14, only in that at least one of fans arranged in the closed space 200 is arranged adjacent a local heat generating portion which locally generates heat, and is arranged so as to locally supply air to the local heat generating portion. In the following, only the different points are described. Thus, the same parts and components as those in the second embodiment are denoted by the same reference numerals and characters, and the explanation of the components is omitted.

The present embodiment will be described by taking, as an example of the local heat generating portion, an electrical component 191 for controlling the light quantity of the light source.

As shown in FIG. 15, in the closed space 200, fans 181 and 183 configuring heat dissipating means and a heat diffusion member, which by convecting the atmosphere in the closed space 200 by air supply, perform at least one of dissipation of the heat of the electrical component 191 to the closed space 200 and transfer of the heat in the atmosphere in the closed space 200 to the exterior housing 4, the frame member 30, and the lid 31, are arranged in such a manner that the air supply directions of the fans are different from each other. The fan 183 is also configured by a small axial fan. The air volumes of the fan 181 and the fan 183 may be different from each other.

For example, in FIG. 15, the fan 183 is arranged in a position which is above the main substrate 160, and which is adjacent the one face 4a and the one face 4d of the exterior housing 4 and adjacent the electrical component 191. Also, the fan 183 is arranged to be inclined with respect to the one face 4a and the one face 4d so that the air supply direction of the fan 183 faces the electrical component 191.

The fan 183 locally supplies air to the adjacent electrical component 191 which locally generates heat, so as to actively dissipate the heat of the electrical component 191 to the closed space 200.

The fan 181 generates thoroughly convection J in the atmosphere in the closed space 200 by supplying air together with the fan 183, as shown in FIG. 15.

Next, the effects of the present embodiment configured in this way will be described.

First, when the connector box 40 is mounted to the housing chamber 45 of the apparatus main body 3 as shown in FIG. 8, the slit 44 of the housing chamber 45 communicates with the slit 63 of the connector box 40 as described above, so that the closed space 200 closed by the exterior housing 4, the frame member 30, and the lid 31 is formed in the inside of the exterior housing 4, the frame member 30, and the lid 31.

Thereafter, when the heat generating portion is driven by the driving or the like of the endoscope 2, the heat generating portion generates heat, so that the atmosphere in the closed space 200 is heated.

At this time, when the fan 181 and the fan 183 are driven, that is, the air supply is started, the air supplied by the fan 181 is sucked by the fan 183, and the air supplied by the fan 183 is sucked by the fan 181, so that the convection J is thoroughly generated in the atmosphere in the closed space 200.

The heat of the heat generating portion is actively dissipated to the atmosphere in the closed space 200 by the convection J, so as to be cooled. That is, a heat dissipation flow H is generated.

Further, the fan 183 locally supplies air to the adjacent electrical component 191, that is, locally generates an air supply flow P toward the electrical component 191, so as to thereby locally and actively dissipate the locally generated heat of the electrical component 191 to the atmosphere in the closed space 200. Thereby, the electrical component 191 is cooled.

Further, the beat in the heated atmosphere in the closed space 200 is actively transferred to the exterior housing 4, the frame member 30, and the lid 31, as a whole, by the convection J generated by the air supplied by the fan 181 and the fan 183. That is, a heat transfer flow D1 is thoroughly generated in the closed space 200. The other effects and the heat flow from the closed space 200 to the outside of the exterior housing 4, the frame member 30, and the lid 31 are the same as those of the second embodiment as described above with reference to FIG. 4, and hence the explanation thereof is omitted.

In this way, in the present embodiment, it is described that the fan 183 is arranged adjacent the electrical component 191 which locally generates heat by being driven, so as to make the air supply direction of the fan 183 directed toward the electrical component 191. Further, it is described that air is locally supplied from the fan 183 to the electrical component 191.

Thereby, the electrical component 191 which locally generates heat can be locally cooled by the air supply flow P, without blocking the convection J. This makes it possible to efficiently and securely cool not only the atmosphere in the closed space 200 but also the electrical component 191.

Therefore, even when the electrical component 191 which locally generates heat is arranged in the closed space 200 closed by the exterior housing 4, the frame member 30, and the lid 31, it is possible to obtain the same effects as those of the above described second embodiment.

Modifications will be described below.

In the present embodiment it is described that two fans of the fan 181 and fan 183 are provided in closed space 200. However, it is needless to say that two or more fans may also be arranged.

Further, the arrangement positions of the fan 181 and the fan 183 are not limited to the positions as described above with reference to FIG. 15, but the fans may be arranged in any positions where the convection J can be thoroughly generated in the atmosphere in the closed space 200, and enable the heat generating portion and the electrical component 191 to be securely cooled.

Further, in the present embodiment, the local heat generating portion which locally generates heat is described by taking, as an example, the electrical component 191, or the like, which controls the light quantity of the light source, but the present invention is not limited to this. It is needless to say that the present invention may be applied to any component that is arranged in the closed space 200 and locally generates heat by the driving of the endoscope 2.

Further, in the first to third embodiments, the endoscope apparatus 1 is described, by taking as an example, the shoulder type industrial endoscope apparatus which is excellent in portability, but the present invention is not limited thereto. It is needless to say that the present invention may be applied to a large-sized industrial endoscope apparatus which has an insertion portion of about 10 m in length, and stores the insertion portion in the apparatus main body.

Further, the present invention is not limited to the industrial endoscope apparatus, and it is needless to say that the present invention may be applied to a medical endoscope apparatus.

Further, the present invention described in above embodiments is not limited to the above described embodiments, and various modifications are possible in an implementation stage within the scope and spirit of the present invention. Further, various stages of the present invention are included in the above described embodiments, and various inventions may be extracted by properly combining the plurality of disclosed constitution elements.

For example, even when several constitution elements are eliminated from all the constitution elements as shown in the embodiments, it is possible to solve the above described problems. When an effect as described as the effect of the present invention is obtained, the configuration in which the constitution elements are eliminated may also be extracted as the present invention.

Having described the embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus comprising:
  an endoscope comprising a thin and long insertion portion having flexibility;
  a connector main body arranged on a proximal end side of the endoscope, the connector main body comprising an exterior housing configured to house a heat generating portion, wherein the exterior housing of the connector main body has an air passage hole that communicates an inner surface of the exterior housing of the connector main body with an outer surface of the exterior housing of the connector main body;
  an apparatus main body comprising an exterior housing, wherein the exterior housing of the apparatus main body has a slit that communicates an inner surface of the exterior housing of the apparatus main body with an outer surface of the exterior housing of the apparatus main body, and wherein the outer surface of the exterior housing of the apparatus main body defines a housing chamber to which the connector main body is configured to be detachably mounted, and wherein the slit is formed in the exterior housing of the apparatus main body at a part where the housing chamber is formed so as to face and communicate with the air passage hole of the exterior housing of the connector main body in a state where the connector main body is mounted to the housing chamber; and
  a fan provided in the exterior housing of the apparatus main body, the fan being configured to supply air to the heat generating portion provided in the exterior housing of the connector main body through the slit and the air passage hole,
  wherein in the state where the connector main body is mounted to the housing chamber, the slit communicates with the air passage hole facing the slit, thereby causing an inner space defined by the inner surface of the exterior housing of the apparatus main body to communicate with an inner space defined by the inner surface of the exterior housing of the connector main body so that one sealed space is formed to preclude movement of air from outsides of the apparatus main body and the connector main body into the one sealed space,
  wherein the fan is configured to generate convection of the air between the inner space of the exterior housing of the apparatus main body and the inner space of the exterior housing of the connector main body which form the one sealed space, and
  wherein heat generated by the heat generating portion is conducted from the inner surface of each of the exterior housing of the apparatus main body and the exterior housing of the connector main body to the outer surface of each of the exterior housing of the apparatus main body and the exterior housing of the connector main body, and radiated from the outer surface of each of the exterior housing of the apparatus main body and the exterior housing of the connector main body.

2. The endoscope apparatus according to claim 1, wherein each of the exterior housing of the connector main body and the exterior housing of the apparatus main body is configured by a heat conducting member which radiates the heat in the atmosphere in the one sealed space in the apparatus main body and the connector main body to the outside of the exterior housing of the connector main body and the exterior housing of the apparatus main body.

3. The endoscope apparatus according to claim 2, wherein the heat conducting member is made of magnesium.

4. The endoscope apparatus according to claim 1,
  wherein in the state where the connector main body is mounted to the housing chamber, the fan is arranged adjacent to the exterior housing of the apparatus main body to face the inner surface of the exterior housing of the apparatus main body, and
  wherein the fan locally transfers heat in the atmosphere in the one sealed space to the exterior housing of the apparatus main body by supplying air to the exterior housing of the apparatus main body.

5. The endoscope apparatus according to claim 1,
  wherein in the state where the connector main body is mounted to the housing chamber, the fan is arranged adjacent to the heat generating portion to face the heat generating portion, and
  wherein the fan dissipates heat generated by the heat generation portion to the one sealed space by supplying air to the heat generating portion.

6. The endoscope apparatus according to claim 1,
  wherein the heat generating portion is configured by a plurality of substrates arranged in the apparatus main body and the connector main body, and
  wherein in the state where the connector main body is mounted to the housing chamber of the apparatus main body, the plurality of substrates are arranged in parallel with each other in the one sealed space.

7. The endoscope apparatus according to claim 6, wherein the fan is provided in a position to overlap with the plurality of substrates in the apparatus main body and the connector main body in the arrangement direction of the plurality of substrates in a plane view.

8. The endoscope apparatus according to claim 1, wherein, by the convection generated by the fan, the heat in the atmosphere in the one sealed space in the exterior housing of the apparatus main body is transferred to the exterior housing of the connector main body and the heat in the atmosphere in the one sealed space in the exterior housing of the connector main body is transferred to the exterior housing of the apparatus main body, thereby permitting the transferred heat to radiate from each of the exterior housing of the connector main body and the exterior housing of the apparatus main body to the outside of the exterior housing of the connector main body and the exterior housing of the apparatus main body.

9. The endoscope apparatus according to claim 1,
wherein a plurality of the fan are provided in the exterior housing of the apparatus main body, and
wherein the plurality of fans are configured to generate convection of the air between the inside of the exterior housing of the apparatus main body and the inside of the exterior housing of the connector main body which form the one sealed space.

10. The endoscope apparatus according to claim 9, wherein, by the convection generated by the plurality of fans, the heat generated by the heat generating portion is conducted from the inner surface of each of the exterior housing of the apparatus main body and the exterior housing of the connector main body to the outer surface of each of the exterior housing of the apparatus main body and the exterior housing of the connector main body, and radiated from the outer surface of each of the exterior housing of the apparatus main body and the exterior housing of the connector main body.

11. The endoscope apparatus according to claim 9, wherein the air supply directions of at least two fans of the plurality of fans are relatively different from each other.

12. The endoscope apparatus according to claim 9,
wherein air volumes of the plurality of fans are different from each other.

13. An endoscope apparatus comprising:
an endoscope comprising a thin and long insertion portion having flexibility;
a connector main body arranged on a proximal end side of the endoscope, the connector main body comprising an exterior housing configured to house a heat generating portion, wherein the exterior housing of the connector main body has an air passage hole that communicates an inner surface of the exterior housing of the connector main body with an outer surface of the exterior housing of the connector main body;
an apparatus main body comprising an exterior housing, wherein the exterior housing of the apparatus main body has a slit that communicates an inner surface of the exterior housing of the apparatus main body with an outer surface of the exterior housing of the apparatus main body, and wherein the outer surface of the exterior housing of the apparatus main body defines a housing chamber to which the connector main body is configured to be detachably mounted, and wherein the slit is formed in the exterior housing of the apparatus main body at a part where the housing chamber is formed so as to face and communicate with the air passage hole of the exterior housing of the connector main body in a state where the connector main body is mounted to the housing chamber; and
a heat diffusion member provided in the exterior housing of the apparatus main body, the heat diffusion member being configured to supply air to the heat generating portion provided in the exterior housing of the connector main body through the slit and the air passage hole,
wherein in the state where the connector main body is mounted to the housing chamber, the slit communicates with the air passage hole facing the slit, thereby causing an inner space defined by the inner surface of the exterior housing of the apparatus main body to communicate with an inner space defined by the inner surface of the exterior housing of the connector main body so that one sealed space is formed to preclude movement of air from outsides of the apparatus main body and the connector main body into the one sealed space,
wherein the heat diffusion member is configured to generate convection of the air between the inner space of the exterior housing of the apparatus main body and the inner space of the exterior housing of the connector main body which form the one sealed space, and
wherein heat generated by the heat generating portion is conducted from the inner surface of each of the exterior housing of the apparatus main body and the exterior housing of the connector main body to the outer surface of each of the exterior housing of the apparatus main body and the exterior housing of the connector main body, and radiated from the outer surface of each of the exterior housing of the apparatus main body and the exterior housing of the connector main body.

14. The endoscope apparatus according to claim 13, wherein the heat diffusion member is a fan.

15. An endoscope apparatus comprising:
an endoscope comprising a thin and long insertion portion having flexibility;
a connector main body arranged on a proximal end side of the endoscope, the connector main body comprising an exterior housing configured to house a heat generating portion, wherein the exterior housing of the connector main body has an air passage hole that communicates an inner surface of the exterior housing of the connector main body with an outer surface of the exterior housing of the connector main body;
an apparatus main body comprising an exterior housing, wherein the exterior housing of the apparatus main body has a slit that communicates an inner surface of the exterior housing of the apparatus main body with an outer surface of the exterior housing of the apparatus main body, and wherein the outer surface of the exterior housing of the apparatus main body defines a housing chamber to which the connector main body is configured to be detachably mounted, and wherein the slit is formed in the exterior housing of the apparatus main body at a part where the housing chamber is formed so as to face and communicate with the air passage hole of the exterior housing of the connector main body in a state where the connector main body is mounted to the housing chamber; and
heat dissipating means provided in the exterior housing of the apparatus main body, the heat dissipating means being configured to supply air to the heat generating portion provided in the exterior housing of the connector main body through the slit and the air passage hole,
wherein in the state where the connector main body is mounted to the housing chamber, the slit communicates with the air passage hole facing the slit, thereby causing an inner space defined by the inner surface of the exterior housing of the apparatus main body to communicate with an inner space defined by the inner surface of the exterior housing of the connector main body so that one sealed space is formed to preclude movement of air from outsides of the apparatus main body and the connector main body into the one sealed space,
wherein the heat dissipating means is configured to generate convection of the air between the inner space of the exterior housing of the apparatus main body and the inner space of the exterior housing of the connector main body which form the one sealed space, and
wherein heat generated by the heat generating portion is conducted from the inner surface of each of the exterior housing of the apparatus main body and the exterior housing of the connector main body to the outer surface of each of the exterior housing of the apparatus main body and the exterior housing of the connector main body, and radiated from the outer surface of each of the exterior housing of the apparatus main body and the exterior housing of the connector main body.

* * * * *